United States Patent [19]

Wilson

[11] Patent Number: 4,769,018
[45] Date of Patent: Sep. 6, 1988

[54] CANNULA ASSEMBLY

[75] Inventor: Dennis S. Wilson, Edwardsburg, Mich.

[73] Assignee: Storz Instrument Company, St. Louis, Mo.

[21] Appl. No.: 73,529

[22] Filed: Jul. 15, 1987

[51] Int. Cl.⁴ .............................................. A61B 17/32
[52] U.S. Cl. .................... 604/283; 604/280; 604/248; 604/158
[58] Field of Search .................. 128/305; 604/91, 171, 604/22, 246, 248, 264, 272, 280, 283, 158

[56] References Cited

U.S. PATENT DOCUMENTS

| 4,137,920 | 2/1979 | Bonnet | 128/305 X |
| 4,345,589 | 8/1982 | Hiltebrandt | 604/264 |
| 4,643,717 | 2/1987 | Cook et al. | 604/22 |
| 4,688,554 | 8/1987 | Habib | 604/282 X |

FOREIGN PATENT DOCUMENTS

| 2855502 | 12/1978 | Fed. Rep. of Germany | 604/158 |
| 2835812 | 2/1980 | Fed. Rep. of Germany | 604/272 |

OTHER PUBLICATIONS

Journal of Arthroscopic and Related Surgery, vol. 3, No. 8 (1987), Aspen Labs advertisement and Karl Storz advertisement.
"What's New", Stryker Surgical advertisement, Aug. 1986.
Surgical Instruments Except Eye Instruments, Storz Instrument Co.-13th Edition (copyright page; pp. 295; 317; 325) Jan. 1977.
Storz Ophthalmic Products (Table of Contents; pp. 9; 22; 23; 26) Jan. 1983.

Primary Examiner—Willis R. Wolfe
Assistant Examiner—Eric R. Carlberg
Attorney, Agent, or Firm—Harness, Dickey & Pierce

[57] ABSTRACT

An improved surgical cannula assembly adapted for receiving and guiding a surgical instrument having an instrument portion insertable through the cannula assembly includes two selectively interconnectable and separable cannula subassemblies. An elongated, longitudinally outer cannula subassembly includes a fluid port extending generally laterally through a portion of the outer cannula subassembly in communication with the interior of the generally hollow outer cannula subassembly. An elongated longitudinally inner cannula subassembly includes an open inner end adapted to be positioned adjacent a surgical sit. A connecting or coupling apparatus is provided for selectively interconnecting the inner and outer cannula subassemblies with one another, in order to define a so-called "full-length" cannula for receiving full-length instruments. The connecting apparatus is also selectively separable in order to disconnect the inner cannula subassembly from the outer cannula subassembly, with the inner cannula subassembly defining a so-called "reduced-length" cannula for receiving reduced-length instruments. At least one valve is interconnected with the outer cannula subassembly in fluid communication with the lateral fluid port to provide fluid communication through the full-length cannula between a fluid flow source and the surgical site.

15 Claims, 5 Drawing Sheets

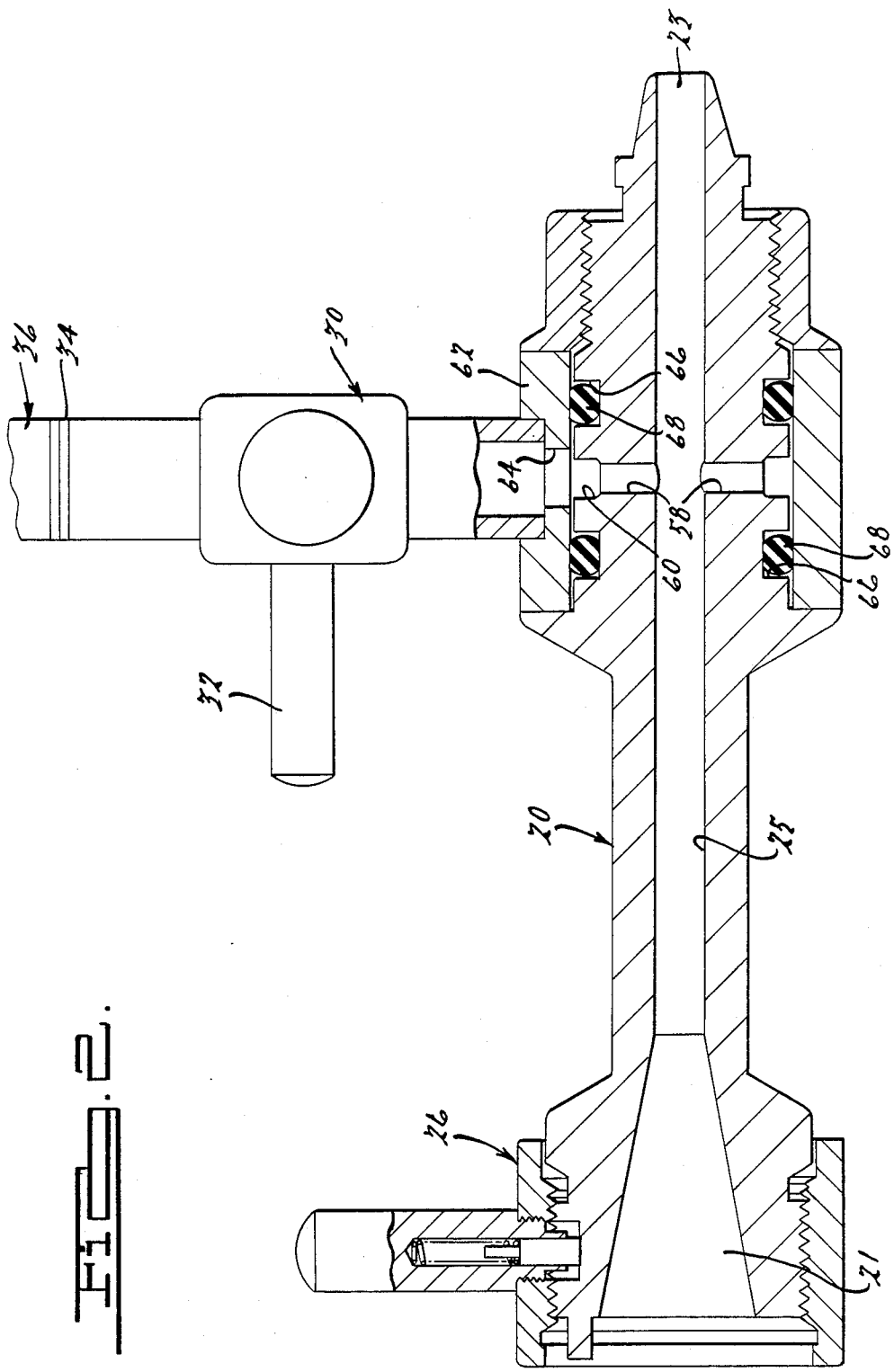

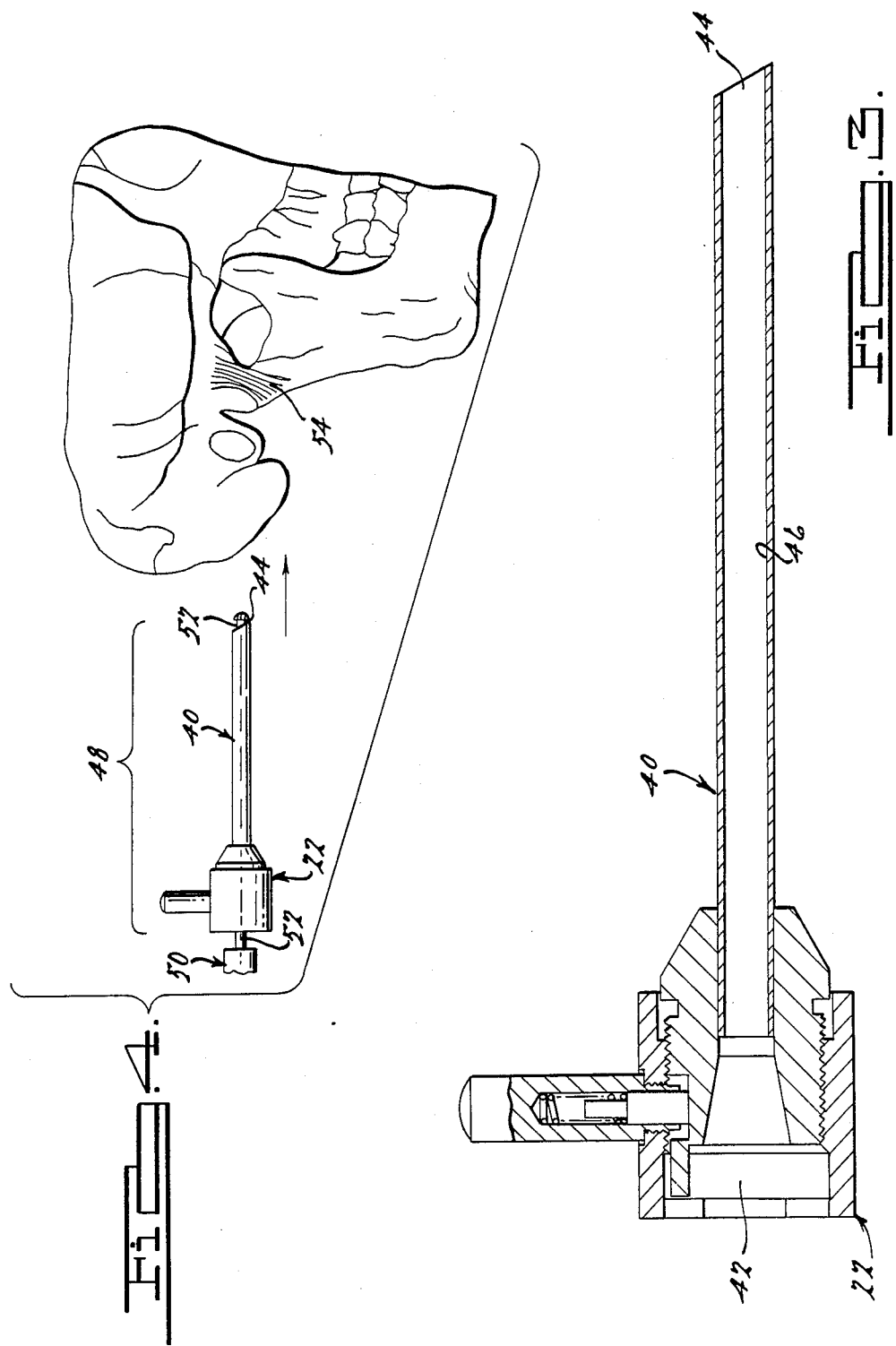

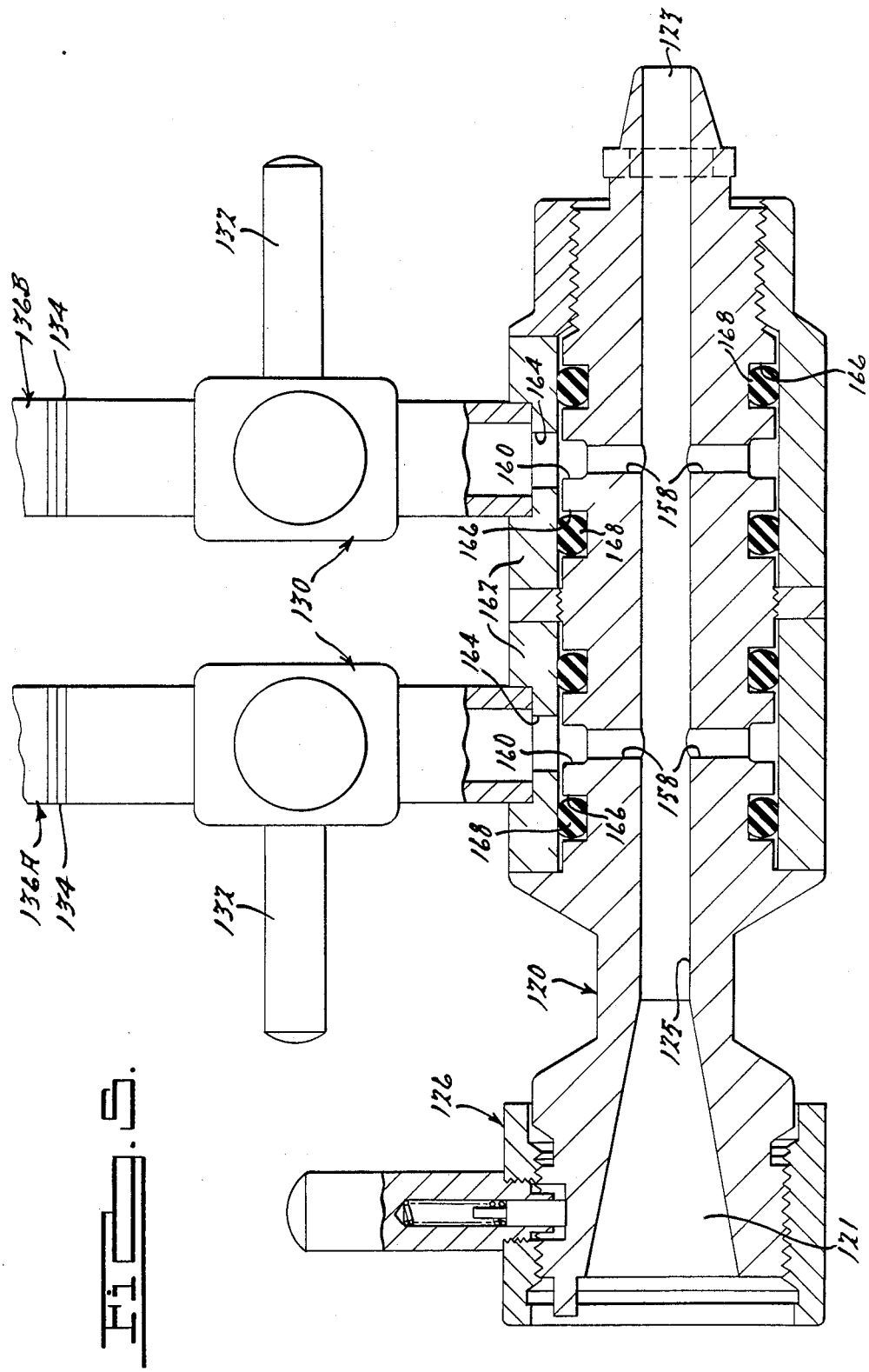

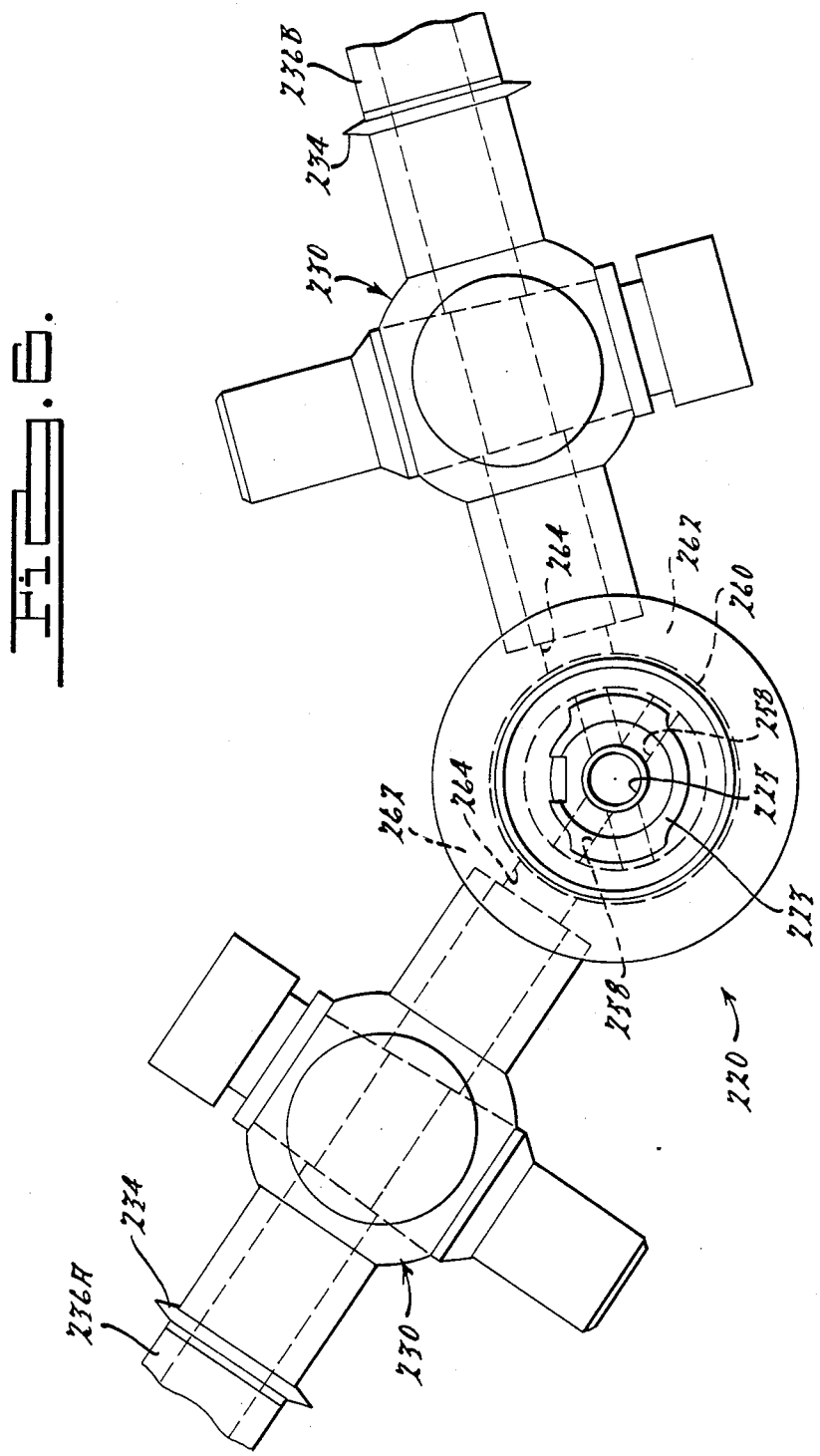

CANNULA ASSEMBLY

BACKGROUND AND SUMMARY OF THE INVENTION

The present invention relates generally to medical-surgical cannula devices adapted for insertion through body tissue and the like surrounding an anatomical site in order to provide a conduit for receiving and guiding surgical instruments through such tissue to the anatomical site, thus allowing various medical or surgical procedures to be performed. In particular, the present invention relates to such a cannula device having two selectively separable and interconnectable cannula subassemblies, thereby allowing different surgical set-ups to be achieved, and allowing medical-surgical instruments of different lengths to be received and guided to the anatomical site, without the necessity of removing and reinserting a cannula device during the procedure. The present invention is particularly advantageous in arthroscopic surgical procedures involving small skeletal joints, such as the temporomandibular joint, for example.

In arthroscopic surgical procedures, a cannula is typically used to provide a conduit for introducing various medical-surgical instruments such as powered shavers, hand-operated cutters, arthroscopes, and the like, into the surgical site through the surrounding tissue. The typical cannula is a relatively thin-walled, stainless steel tube, typically having a clamping or coupling device on its outer end. Such a clamping device allows instruments, such as obturators, arthroscopes, etc., to be securely attached to the cannula, with their inner ends protruding from the open inner end of the cannula.

An obturator is inserted through the cannula and locked in place by the clamping or coupling device, with the inner end of the obturator forcibly pushing the surrounding tissue aside as the cannula-obturator assembly is inserted through the body tissue to a position with its inner end adjacent the surgical site. Once the cannula-obturator assembly is properly positioned, the obturator is removed, and the cannula is left in place to provide a clear path or conduit through the body tissue to the surgical site. An arthroscope can then be inserted through the cannula and securely clamped or coupled to its outer end in order to inspect and view the surgical site during the surgical procedure.

Typically, the portions of the instruments that are insertable through the cannula are of a generally standardized length, usually approximately ten centimeters long. Thus, the cannula must also be approximately ten centimeters long in order to function to provide a path or conduit through the body tissue to the surgical site. However, because of the recent development of the use of arthroscopics in small skeletal joints, such as the temporomandibular joint, for example, arthroscopes, shavers, and other instruments necessary in such arthroscopic procedures must be small enough to be used in such small skeletal joints. The reduced size of these instruments (with insertable instrument portions of approximately 5 to 6 centimeters) frequently results in an undesirable reduction in the strength and durability of their components.

In addition, because the above-mentioned standardized length of such instruments portions is frequently much longer than necessary to operate in such small skeletal joints, the extra undesirable length results in the outer open end or portal being inordinately spaced away from the patient's skin. Such unwanted extra spacing from the patient's skin frequently presents difficulties in taping or otherwise securing the cannula to the patient, or in other fixed positions relative to the patient, in order to restrict its movement during surgical procedures.

Because of the above, it has been found that a shorter cannula (typically about 5 centimeters long) would eliminate many of the above-discussed disadvantages in surgical procedures involving the temporomandibular joint or other small skeletal joints by providing the ease and convenience of secure taping or other anchoring of the cannula device, while also allowing for the use of shorter, and thus stronger, shavers, abraders, trimmers, and other surgical instruments. It is deemed highly undesirable, however, to remove a longer cannula required for use with certain obturators, arthroscopes, or other longer instruments, and to reinsert a shorter cannula when the shorter and stronger surgical instruments are required during the same surgical procedure. This is because the removal and reinsertion of a cannula increases the risk of unnecessary trauma or damage to the patient's surrounding body tissue, muscles, and nerves during cannula insertion.

In addition to the above-discussed problems associated with relatively longer or shorter surgical instruments, some surgical procedures require the connection of a source of fluid flow for either introducing a fluid to the surgical site, or for withdrawing fluids from the surgical sites, thus typically requiring additional cannula length for fluid connections, shut-off or control valves, and the like. However, because of the above-mentioned risk of trauma and damage to the surrounding body tissue, muscles, and nerves, it is undesirable to remove and reinsert cannulas of different lengths or configurations when fluid introduction or withdrawal and the use of above-mentioned shorter and stronger surgical instruments are required or deemed desirable in the same surgical procedure.

The present invention seeks to provide a cannula assembly that overcomes the above-discussed problems by allowing the use of fluid introduction or withdrawal apparatus, as well as surgical instruments such as arthroscopes, obturators, powered shavers and abraders, and the like, having instrument portions of different lengths insertable through the cannula assembly, without the necessity of removing and reinserting cannulas of different lengths and configurations during the same surgical procedure.

According to the present invention, an improved surgical cannula assembly adapted for receiving and guiding a surgical instrument having an instrument portion insertable through the cannula assembly includes two selectively interconnectable and separable cannula subassemblies. An elongated, longitudinally outer cannula subassembly is generally hollow and includes open longitudinally inner and outer ends and a fluid port extending generally laterally through a portion of the outer cannula subassembly. The fluid port is in communication with the interior of the generally hollow outer cannula subassembly in order to allow for the introduction or withdrawal of fluids therethrough. An elongated and generally hollow longitudinally inner cannula subassembly includes open longitudinally inner and outer ends, with the open inner end of the inner cannula assembly being adapted to be positioned adjacent a surgical site. A connecting or coupling apparatus is provided for selectively interconnecting the inner and outer cannula subassemblies with one another, with their respective hollow interiors in communication with one another, in order to define a so-called "full-length" cannula. The connecting or coupling means is also selectively separable in order to disconnect the inner cannula subassembly from the outer cannula subassembly, with the inner cannula subassembly defining a so-called "reduced-length" cannula. The connecting or coupling apparatus includes sealing means for sealing the interconnected inner and outer cannula subassemblies in a fluid-tight relationship with one another.

At least one valve is provided and is interconnected with the outer cannula subassembly in fluid communication with the lateral fluid port, with the valve being selectively interconnectable in fluid communication with a source of fluid flow and operable to provide fluid communication through the full-length cannula between the fluid flow source and the surgical site.

Thus the above-mentioned full-length cannula is adapted for receiving and guiding a surgical instrument having a full-length instrument portion insertable through the full-length cannula and for selectively introducing or withdrawing fluids to or from the surgical site. The above-mentioned reduced-length cannula is adapted for receiving and guiding surgical instruments having reduced-length instrument portions insertable therethrough when the insertion of full-length instrument portions and the introduction or withdrawal of fluid from the surgical site is not deemed necessary or desirable, or when it is desirable or necessary to use instruments having stronger reduced-length instrument portions insertable through the reduced-length cannula. Such capabilities are provided by the present invention with only a single insertion of a cannula through the surrounding tissue, muscles, or nerve areas surrounding the surgical site during a given surgical procedure.

Preferably, the above-mentioned valve is interconnected with the outer cannula subassembly for selective rotatable movement of the laterally outwardly-extending valve assembly about the lateral periphery of the outer cannula subassembly to any of a number of laterally outward-extending orientations. During such selective rotatable movement and positioning, the valve is maintained in fluid communication with the fluid port extending laterally through the outer cannula subassembly. In some forms of the present invention, more than one of such valves is provided on the outer cannula subassembly in order to allow for the selective introduction and withdrawal of fluids from the surgical site without the necessity of disconnecting and reconnecting various fluid flow sources. In addition, in such multi-valve embodiments of the present invention, the selective introduction of dissimilar fluids, either simultaneously or at different times, can also be accomplished.

Additional objects, advantages, and features of the present invention will become apparent from the following description and the appended claims, taken in conjunction with the accompanying drawings.

BRIEF DESCRIPTION OF THE DRAWINGS

FIG. 2 is a longitudinal cross-sectional view of the outer cannula subassembly of the exemplary cannula assembly shown in FIG. 1.

FIG. 3 is a longitudinal cross-sectional view of the inner cannula subassembly of the exemplary cannula assembly shown in FIG. 1.

FIG. 4 diagrammatically represents the use of the disconnected inner cannula subassembly in order to define a reduced-length cannula for use in surgical procedures on small skeletal joints, such as the temporomandibular joint diagrammatically illustrated in FIG. 4.

FIG. 5 illustrates a longitudinal cross-sectional view similar to that of FIG. 2, but showing an alternate embodiment of the outer cannula subassembly having two fluid valves longitudinally spaced apart from one another on the outer cannula subassembly.

FIG. 6 is an end view of still another alternate outer cannula subassembly, which is similar to that shown in FIGS. 1 and 2, but having a pair of fluid valves interconnected with the outer cannula subassembly, generally at the same longitudinal position thereon, but extending laterally at an angular relationship with one another.

DETAILED DESCRIPTION OF THE PREFERRED EMBODIMENTS

Figure 1:
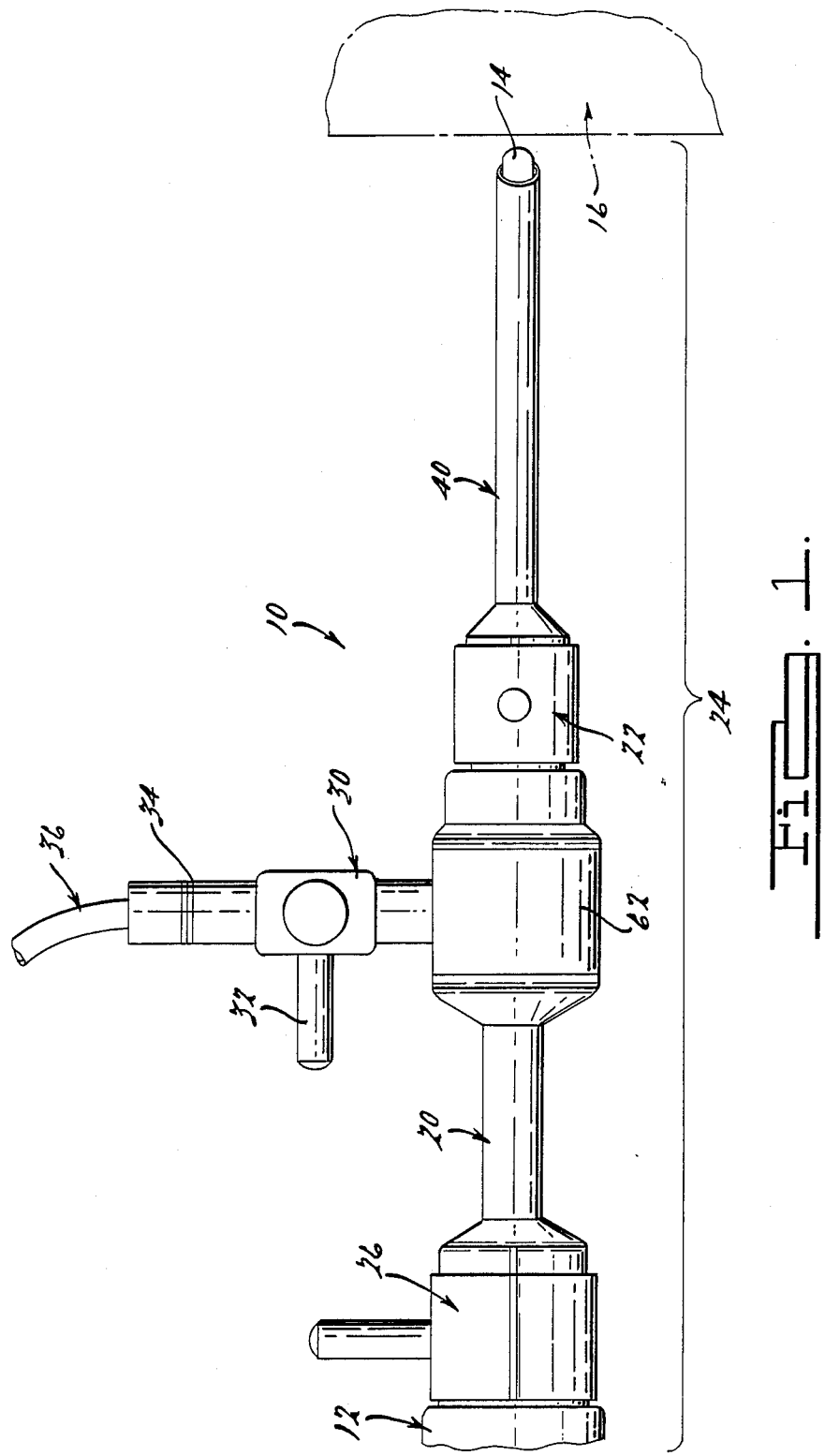
FIG. 1 is an elevational view of an exemplary cannula assembly according to the present invention, with its inner and outer subassemblies connected with one another in order to form a full-length cannula, with its inner end shown positioned generally adjacent a surgical site shown diagrammatically.

FIGS. 1 through 6 illustrate various exemplary embodiments of a cannula assembly according to the present invention. One skilled in the art will readily recognize from the following discussion, and the accompanying drawings and claims, that the principles of the present invention are equally applicable to cannulas other than those of the particular configuration illustrated in the drawings.

FIG. 1 illustrates an exemplary cannula assembly 10 adapted for providing a path or conduit through body tissue, muscles, or nerves, and for receiving and guiding a surgical instrument 12 having a full-length instrument portion 14 insertable into the cannula assembly for performing medical or surgical procedures at a surgical site 16. The cannula assembly 10 includes an outer cannula subassembly 20 and an inner cannula subassembly 40 when fully assembled. The outer cannula subassembly 20 includes an open outer end 21, an open inner end 23, and a generally hollow interior 25 extending therethrough, as shown in FIG. 2. The inner cannula subassembly, shown in cross-section in FIG. 3, also includes an open outer end 42, an open inner end 44, and a hollow interior 46.

A coupling apparatus 26 is provided for selectively interconnecting the outer cannula subassembly 20 with the inner cannula subassembly 40 in order to define the overall, full-length cannula 24 illustrated in FIG. 1. The coupling apparatus 26 is a substantially leakproof coupler well-known in the medical art and is thus not described in detail herein.

The outer cannula subassembly 20 also includes a valve 30 interconnected therewith, and in fluid communication with one or more laterally-extending ports 58 in order to provide fluid communication between the valve 30 and the hollow interior 25, as shown in FIG. 2. The valve 30 is equipped with a valve operator 32 for selectively providing or preventing fluid communication between the hollow interior 25 and a fluid flow source 36. The fluid flow source 36 is selectively interconnectable with, and disconnectable from, the valve 30 by way of a fluid connector device 34. Thus, when connected to the fluid flow source 36, the full-length cannula 24 can be employed for introducing fluids to, or withdrawing fluids from, the surgical site 16, as deemed desirable or necessary in a particular surgical procedure.

As shown in FIGS. 3 and 4, the disconnected inner cannula subassembly 40 effectively defines a reduced-length cannula 48 for receiving and guiding medical or surgical instruments 50 having reduced-length instrument portions 52 protruding from the open inner end 44, which is adapted to be positioned adjacent a surgical or anatomical site, such as the temporomandibular joint 54, as illustrated diagrammatically in FIG. 4.

As discussed above, the need for reduced-length surgical instruments such as arthroscopes, shavers, abraders, and the like, in surgical procedures on small skeletal joints such as the temporomandibular joint 54, has become more pronounced as a result of the development of arthroscopic surgical procedures in such surgical operations. The reduced-length cannula 48, defined by the disconnected inner cannula subassembly 40 allows for the use of instruments 50 having reduced-length instrument portions 52, which are accordingly stronger, more durable, and more maneuverable than the instruments 12 with their full-length instrument portions 14 shown diagrammatically in FIG. 1.

Preferably, the above-discussed valve 30 on the outer cannula subassembly 20 is rotatably movable to any of a number of laterally outwardly-extending orientations about the lateral periphery of the outer cannula subassembly 20. In the preferred embodiments of the present invention, such rotatable positioning or orienting of the valve 30 is accomplished by way of a rotatable collar member 62 generally surrounding the outer cannula subassembly 20 and having a laterally-extending collar opening 64 therethrough. The collar member 62 is positioned on the outer cannula subassembly such that its collar opening 64 is in fluid communication with an annular recessed portion 60 extending about the lateral periphery of the outer cannula subassembly 20 and in communication with the laterally-extending ports 58 therethrough.

A pair of annular recessed portions 66 are preferably provided on opposite longitudinal sides of the annular recessed portion 60 for housing a pair of sealing members 68, which are provided for sealing engagement with the outer cannula subassembly 20 and the rotatable collar member 62 in a generally fluid-tight relationship therebetween. Thus, the valve 30, which is interconnected with the rotatable collar member 62 in fluid communication with the collar opening 64, can be selectively rotated to virtually any laterally outwardly-extending orientation relative to the outer cannular subassembly 20. This facilitates the ease and convenience of connecting the fluid flow source 36 with the full-length cannula 24 at a position that does not interfere with the required procedures in a surgical operation, and without interfering with the patient or other surgical apparatus in the surrounding area.

In FIG. 5, an alternate embodiment of the present invention is illustrated, wherein an alternate outer cannula subassembly 120 is generally similar to the outer cannula subassembly 20 shown in FIGS. 1 and 2, with certain exceptions discussed below. Because of such similarity in either function or configuration, the various components and elements of the outer cannula subassembly 120 are indicated by reference numeral one-hundred higher than those of functionally or structurally similar corresponding components or elements of the outer cannula subassembly 20 shown in FIGS. 1 and 2.

The outer cannula subassembly 120 includes at least a pair of valves 130 and a corresponding number of respective laterally-extending ports 58. The valves 130 are each in fluid communication with the respective laterally-extending ports 58, and rotatably movable around the outer cannula subassembly 120 by way of respective rotatable collar members 162, each having a collar opening 164 extending therethrough, in a manner similar to that shown in connection with the outer cannula subassembly 20 in FIG. 2. Also similar to the arrangement shown in FIG. 2, the outer cannula subassembly 120 has an annular recessed portion 160 extending around, and in fluid communication with, the respective laterally-extending ports 158.

Thus, in a manner similar to that discussed above in connection with FIG. 2, each of the valves 130 can be selectively interconnected with either similar or dissimilar fluid flow sources 136A and 136B for selectively providing fluid communication through a full-length cannula having the outer cannula subassembly 120 thereon, between the fluid flow sources 136A and 136B and the surgical site. Also, in a manner similar to that described above in connection with FIG. 2, each of the valves 130 is rotatably positionable in any of a number of longitudinally outwardly-extending orientations, independently of the other valve 130. This arrangement thus provides the flexibility of multiple fluid flow source connections while maintaining the capability of independently positioning the valves 130 in orientations that are convenient for the use and anchoring of a full-length cannula in a particular surgical arrangement or configuration.

FIG. 6 illustrates still another alternate embodiment of the present invention, wherein an outer cannula subassembly 220 is employed in a full-length cannula, similar to that shown and described in connection with FIGS. 2 and 5, but with certain exceptions discussed below. Because of the various similarities both in function and configuration among the various components or elements of the outer cannula subassembly 220 with the outer cannula subassemblies 20 and 120 discussed above, the various components or elements of the outer cannula subassembly 220 are indicated by reference numerals similar to those in FIGS. 2 and 5, but with two-hundred prefixes.

In FIG. 6, the outer cannula subassembly 220 includes at least a pair of valves 230 interconnected with a single rotatable collar member 262, similar to each of the rotatable collar members 162 in FIG. 5 and the rotatable collar member 62 in FIG. 2. Thus, each of the valves 230, which are disposed at a laterally-spaced, angular relationship with one another, are in fluid communication with the hollow interior 225 of the outer cannula subassembly 220 in a manner similar to that described above in connection with the outer cannula subassemblies 20 and 120. In such an arrangement, the flexibility of connecting either similar or dissimilar fluid flow sources 236A and 236B to the outer cannula subassembly 220 is maintained, while still providing the capability of rotating the valves 230 about the lateral periphery of the outer cannula subassembly 220 to a convenient position for the surgical operation being performed. Unlike the valve 130 in FIG. 5, however, the valves 230 in FIG. 6 rotate together, in a fixed angular relationship with one another, and not independently from one another. In this regard, the specific angular relationship shown in FIG. 6 is not critical and can be any desired angle from 0 to 180 degrees.

The foregoing discussion discloses and describes exemplary embodiments of the present invention. One skilled in the art will readily recognize from such discussion, and from the accompanying drawings and claims, that various changes, modifications and variations may be made therein without departing from the spirit and scope of the invention as defined in the following claims.

What is claimed is:

1. An improved surgical cannula assembly adapted for receiving and guiding a surgical instrument having an instrument portion insertable through said cannula assembly, said improved cannula assembly comprising:

an elongated, generally hollow longitudinally outer cannula subassembly having open longitudinally inner and outer ends, said outer cannula subassembly having a fluid port extending generally laterally through a portion thereof, said fluid port being in communication with the interior of said generally hollow outer cannula subassembly;

an elongated, generally hollow longitudinally inner cannula subassembly having open longitudinally inner and outer ends, said open inner end of said inner cannula subassembly being adapted to be positioned adjacent a surgical site;

connection means for selectively interconnecting said inner and outer cannula subassemblies with one another with their respective hollow interiors in communication with one another in order to define a full-length cannula and for selectively disconnecting said inner and outer cannula subassemblies from one another in order to define a reduced-length cannula, said connection means including sealing means for sealing said interconnected inner and outer cannula subassemblies in a fluid tight relationship with one another; and a valve interconnected with said outer cannula subassembly in fluid communication with said fluid port in said outer cannula subassembly, said valve being selectively interconnectable in fluid communication with a source of fluid flow and being selectively operable to provide fluid communication through said full-length cannula between said fluid flow source and the surgical site when said open inner end of said inner cannula subassembly is positioned adjacent the surgical site, said full-length cannula being adapted for receiving and guiding a surgical instrument having a full-length instrument portion insertable through said full-length cannula, and said reduced-length cannula being adapted for receiving and guiding a surgical instrument having a reduced-length instrument portion insertable through said reduced-length cannula, the full-length instrument portion being of a sufficient length to protrude from said open inner end of said inner cannula subassembly when inserted through said full-length cannula, and the reduced-length instrument portion being of a sufficient length to protrude from said open inner end of said inner cannula subassembly when inserted through said reduced-length cannula but being of an insufficient length to protrude from said open inner end of said inner cannula subassembly when inserted into said full-length cannula, said improved cannula assembly thereby allowing surgical instruments having instrument portions of different lengths to be used interchangeably, and allowing the use of said fluid flow source, in a surgical procedure without removing said open inner end of said inner cannula subassembly from its position adjacent the surgical site.

2. A cannula assembly according to claim 1, wherein said valve extends generally laterally outwardly from the lateral periphery of said outer cannula subassembly, said cannula assembly further including valve positioning means for selectively moving said valve about the lateral periphery of said outer cannula subassembly to any of a number of laterally outwardly-extending orientations relative to said outer cannula subassembly, said valve positioning means maintaining said valve in fluid communication with said fluid port in said outer cannula subassembly in any of said laterally outwardly-extending orientations.

3. A cannula assembly according to claim 2, wherein said valve positioning means includes an inwardly-recessed portion extending around the lateral periphery of said outer cannula subassembly in fluid communication with said fluid port, and a collar member generally surrounding said inwardly-recessed portion and selectively movable therearound, said collar member having a collar opening extending generally laterally therethrough and longitudinally aligned for fluid communication with said inwardly-recessed portion at any position of said collar member around the lateral periphery of said outer cannula subassembly, said valve being interconnected with said collar member for movement therewith and being in fluid communication with said collar opening.

4. A cannula assembly according to claim 3, wherein said valve positioning means further includes fluid sealing means for sealingly engaging said collar member and said outer cannula subassembly on opposite longitudinal sides of said inwardly-recessed portion.

5. A cannula assembly according to claim 1, wherein said outer cannula subassembly has at least a pair of said fluid ports extending generally laterally therethrough and longitudinally spaced from one another, said cannula assembly including one of said valves interconnected with said outer cannula assembly in fluid communication with each of said fluid ports.

6. A cannula assembly according to claim 5, wherein each of said valves extends generally outwardly from the lateral periphery of said outer cannula subassembly, said cannula assembly further including valve positioning means for selectively moving each of said valves independently about the lateral periphery of said outer cannula subassembly to any of a number of laterally outwardly-extending orientations relative to said outer cannula subassembly, said valve positioning means maintaining each of said valves in fluid communication with its respective fluid port in said outer cannula subassembly in any of said laterally outwardly-extending orientations.

7. A cannula assembly according to claim 6, wherein said valve positioning means includes an inwardly-recessed portion extending around the lateral periphery of said outer cannula subassembly in fluid communication with each of said fluid ports, and a collar member generally surrounding each of said inwardly-recessed portions and selectively movable therearound, each of said collar members having a collar opening extending generally laterally therethrough and longitudinally aligned for fluid communication with the respective inwardly-recessed portion at any position of said collar member around the lateral periphery of said outer cannula subassembly, one of said valves being interconnected with each of said collar members for movement therewith and being in fluid communication with the respective collar opening therethrough.

8. A cannula assembly according to claim 7, wherein said valve positioning means further includes fluid sealing means for sealingly engaging each of said collar members and said outer cannula subassembly on opposite longitudinal sides of the respective inwardly-recessed portion.

9. A cannula assembly according to claim 1, further including at least a pair of said valves interconnected with outer cannula assembly in fluid communication with said fluid port.

10. A cannula assembly according to claim 9, wherein each of said valves extends generally outwardly from the lateral periphery of said outer cannula subassembly, said cannula assembly further including valve positioning means for selectively moving said valves about the lateral periphery of said outer cannula subassembly to any of a number of laterally outwardly-extending orientations relative to said outer cannula subassembly, said valve positioning means maintaining each of said valves in fluid communication with said fluid port in said outer cannula subassembly in any of said laterally outwardly-extending orientations.

11. A cannula assembly according to claim 10, wherein said valve positioning means includes an inwardly-recessed portion extending around the lateral periphery of said outer cannula subassembly in fluid communication with said fluid port, and a collar member generally surrounding said inwardly-recessed portion and selectively movable therearound, said collar member having at least a pair of collar openings extending generally laterally therethrough and longitudinally aligned for fluid communication with said inwardly-recessed portion at any position of said collar member around the lateral periphery of said outer cannula subassembly, each of said valves being interconnected with said collar member for movement therewith and being in fluid communication with one of said collar openings.

12. A cannula assembly according to claim 11, wherein said valve positioning means further includes fluid sealing means for sealingly engaging said collar member and said outer cannula subassembly on opposite longitudinal sides of said inwardly-recessed portion.

13. A cannula assembly according to claim 1, wherein said outer cannula subassembly includes coupling means on its outer end for releasable coupling interconnection with a surgical instrument having said full-length instrument portion thereon.

14. A cannula assembly according to claim 1, wherein said outer cannula subassembly includes coupling means on its outer end for releasable coupling interconnection with an obturator having an obturator portion insertable through said full-length cannula to a position protruding from said open inner end of said inner cannula subassembly.

15. A cannula assembly according to claim 1, wherein said outer cannula subassembly includes coupling means on its outer end for releasably coupling interconnection with an arthroscope having an arthroscope portion insertable through said full-length cannula to a position generally adjacent said open inner end of said inner cannula subassembly.

* * * * *

UNITED STATES PATENT AND TRADEMARK OFFICE
CERTIFICATE OF CORRECTION

PATENT NO. : 4,769,018

DATED : September 6, 1988

INVENTOR(S) : Dennis S. Wilson

It is certified that error appears in the above-identified patent and that said Letters Patent is hereby corrected as shown below:

Abstract, line 12, "sit" should be --site--.

Column 5, line 52, "cannular" should be --cannula--.

Signed and Sealed this

Thirty-first Day of October, 1989

Attest:

DONALD J. QUIGG

Attesting Officer

Commissioner of Patents and Trademarks